United States Patent [19]

Inlow et al.

[11] Patent Number: 5,372,943
[45] Date of Patent: Dec. 13, 1994

[54] LIPID MICROEMULSIONS FOR CULTURE MEDIA

[75] Inventors: Duane Inlow; Brian Maiorella, both of Oakland, Calif.

[73] Assignee: Cetus Corporation, Emeryville, Calif.

[21] Appl. No.: 90,568

[22] Filed: Jul. 12, 1993

Related U.S. Application Data

[63] Continuation of Ser. No. 829,610, Jan. 30, 1992, abandoned, which is a continuation of Ser. No. 248,830, Sep. 23, 1988, abandoned, which is a continuation-in-part of Ser. No. 77,189, Jul. 24, 1987, abandoned.

[51] Int. Cl.$^5$ ............................................ C12N 5/00
[52] U.S. Cl. ............................ 435/240.31; 435/240.1; 435/240.3; 252/49.5; 252/302; 428/402.2
[58] Field of Search ............. 435/240.1, 240.3, 240.31; 252/49.5, 302; 428/407.2

[56] References Cited

U.S. PATENT DOCUMENTS

| | | |
|---|---|---|
| Re. 30,985 | 6/1982 | Cartaya ............................ 435/240 |
| 4,173,516 | 11/1979 | Katinger et al. . |
| 4,259,449 | 3/1981 | Katinger et al. . |
| 4,311,798 | 1/1982 | Katinger et al. . |
| 4,485,029 | 11/1984 | Kato et al. ............................ 252/106 |
| 4,533,637 | 8/1985 | Yamane et al. . |
| 4,649,117 | 3/1987 | Familletti . |
| 4,657,866 | 4/1987 | Kumar . |

FOREIGN PATENT DOCUMENTS

| | | |
|---|---|---|
| 127839 | 12/1984 | European Pat. Off. . |
| 62-074284 | 4/1987 | Japan . |

OTHER PUBLICATIONS

Yamane, et al., 1981, *Proc. Japan Acad.*, 57B(10):385–389.

Iscove, In Barnes, et al., (eds), 1984, *Methods for Serum-Free Culture Of Neuronal and Lymphoid Cells*, :169–185.

Goodwin et al., In Kurstak, et al., (eds), *Invertebrate System In Vitro*, 1980, :493–508.

Brooks et al., In "Invertebrate Systems in Vitro", eds Kurstak et al., Elsevier, Amsterdam (1980), pp. 67–77.

Mizraki, J. Clinical Microbiol. 2(1):11–13 (1975).

The Merck Index 1983 Merck & Co. Inc. 1983 Rahway N.J.

Kirk Othmer Encyclopedia of Chemical Technology vol. 13 1967 Wiley & Sons Inc. N.Y. pp. 440, 441, 445, 446, 453, 454.

Ryan et al., Experimental Cell Research 172:318–328 (1987).

Kilburn, et al., 1968, *Biotech. & Bioengin.*, 10:801–814.

Mizrahi, 1984, *Develop. Biol. Standard*, 55:93–102.

McCutcheon's Emulsifiers & Detergents (published by the McCutcheon Division of MC Publishing Co., pp. 253–254.

Summers, et al., 1988, *Texas Agricultural Experiment Bulletin No. 1555*, Texas A & M Univ.

Gardiner et al., 1975, *J. Invert. Pathol.*, 25:363.

Vaughn, et al., 1976, *TCA Manual*, 3(1).

Yunker, et al., 1967, *Science*, 155:1565–1566.

Marks, In Kruse, et al., (eds.), *Tissue Culture Methods & Appl.*, 1973:153–156.

Goodwin, 1975, *In Vitro*, 11:369–378.

Goodwin, et al., 1978, *In Vitro*, 14:485–494.

Hink, 1970, *Nature*, (London), 226:466–467.

(List continued on next page.)

*Primary Examiner*—Jasemine C. Chambers
*Attorney, Agent, or Firm*—Philip J. McGarrigle, Jr.; Paul B. Savereide; Robert P. Blackburn

[57] ABSTRACT

Lipid microemulsions which can be added to cell culture media to provide essential lipids in a bioavailable form and their components are disclosed. Methods to disperse lipids in culture media by the use of one or more emulsifiers are described. Further disclosed are media which support growth of cells and production of recombinant, viral and/or native products wherein lipids are supplied in the form of microemulsion.

13 Claims, 2 Drawing Sheets

OTHER PUBLICATIONS

Hansen, In Maramorosch (ed.)., *Invertebrate Tissue Culture Research Appl.*, 1976, :77–99.

Weiss, et al., 1981, *In Vitro*, 17(6):495–502.

Weiss, et al., 1986, *CRC Press*, :70–72.

Editions of McCutcheon's Emulsifiers & Detergents (published by McCutcheon Div. of MC Pub. Co., 175 Rock Rd, Glenn Rock, N.J., USA).

Yamane, et al., 1981, *Exp. Cell. Res.*, 134:470.

Yamane et al., In Kohono et al., (eds.), *International Symposium on Clinical Potentials and Interferons in Viral Disease & Malignant Tumors*, 1981 :355–364.

Murashige, et al., 1962, *Physio. Plant*, 15:473.

Gamborg, 1968, *Exp. Cell Res.*, 50:151.

Gamborg, et al., 1976, *In Vitro*, 12:473.

Metcalf, 1970, *J. Cell Physiol.*, 76:89.

Summers, et al., 1985, *Banbury Report: Genetically Altered Viruses in the Environment*, 22:319–329.

Granados, et al., (eds.) *The Biology of Baculoviruses*, (CRC Press 1986).

Vaughn, 1981, *Adv. Cell. Cult.*, 1:281.

Vaughn, 1976, *J. Invert. Pathol.*, 1976, 28:233.

Vaughn, In Maramorosch (eds.), *Invert. Tissue Culture: Res. Applics.*, 1976 :295.

Vaughn, In, Barigozzi (eds.), *Proc. of Internal. Colloq. Invert. Tissue Cult.* (2nd Tremezzo, 1967), :119 (1968).

Weiss et al., In Granadoes et al., (eds.) *The Biology of Baculoviruses*, 1986, II:Practical Application for Insect Control:63–87.

Vaughn, et al., 1977, *In Vitro*, 13:213–217.

Smith, et al., 1979, *J. Virol*, 30:828–838.

Smith, et al., 1980, *J. Virol*, 33:311–319.

Smith, et al., 1978, *J. Virol*, 89:517–527.

Summers, et al., 1987, *Texas Agricultural Experiment Bulletin No. 1555*, Texas A & M Univ.

Ryan, P. A., et al., *Exper. Cell Research*, 1987, 172:318–328.

Bettger, W. J., et al., 1981, *PNAS USA*, 78:5588–5592.

Glassy, M. C., et al., 1988, *Biotech & Bioengin.*, 32:1015–1028.

Barnes, D. W., et al., 1984, *Methods for Serum-Free Culture of Neuronal and Lymphoid Cells*, 4:169–185.

Hink, W. F., *Annual Meeting Abstracts*, p. 177 "Growth of TN-368 Insect Cells In Serum-Free Media", Ohio State University, Columbus Ohio.

Tramper, J., et al., 1986, *Enzyme Microb. Technol.*, 8:33.

FIG. 1

LIPID MICROEMULSIONS FOR CULTURE MEDIA

BACKGROUND OF THE RELATED APPLICATION

This application is a file wrapper continuation of application Ser. No. 07/829,610, filed Jan. 30, 1992, now abandoned which was a file wrapper continuation of application Ser. No. 07/248,830, filed Sep. 23, 1988, now abandoned, which was a continuation-in-part of application Ser. No. 07/077,189, filed Jul. 24, 1987, now abandoned.

FIELD OF THE INVENTION

This invention is in the field of fermentation and cell culture. More particularly, the invention concerns cell culture media wherein lipids are supplied in the form of microemulsions and methods to disperse lipids in cell culture media.

BACKGROUND

Lipids are an apparently essential requirement for most animal cell culture. [See Yamane et al., *Proc. Japan Acad.* 57B(10):385-389 at p. 388 (1981); and Iscove, "Culture of Lymphocytes and Hemopoietic Cells in Serum-Free Medium," In Barnes et al. (eds.), *Methods for Serum-Free Culture of Neuronal and Lymphoid Cells*, pp. 169-185 (1984), where it is stated at page 170: "If the experience with lymphocytes and hemopoietic cells can be extrapolated, lipids may turn out to be a universal requirement for freshly explanted cells."] Specific lipid requirements have been identified for mammalian cell lines (CHO) useful for recombinant protein expressing [Ham, *Proc. Natl. Proc. Nat. Acad. Sci.*, 1965 53:288], for insect cell lines (Sf9 [Wilke, et al., 1980, *Develop. Biol. Standard,* 46:29-37] and for antibody secreting cell lines [Kawamoto et al., 1983 *Analytical Biochem.* 130:445-453]. The direct addition of lipids to media is not practical due to their low solubility. Conventionally, in serum-containing media, lipids are provided to the medium in the serum wherein the lipids are carried as water soluble lipoproteins; whereas conventionally, in serum-free media, lipids are carried by albumin to which the lipid is coupled through a process employing a solvent, such as chloroform. [Goodwin et al., In Kurstak et al., (eds.), *Invertebrate Systems In Vitro*, pp. 493-508 (1980); Iscove, id.].

Although conventional culture media have been generally prepared by adding serum in large amounts (about 5 to 20%), the use of serum has a number of disadvantages including (1) expense, in that, more than half of the cost of the media is usually occupied by the costs of the sera; (2) time necessary to check quality of sera which may vary from lot to lot and can be contaminated with mycoplasma or virus; and (3) downstream purification problems, in that, sera can contain various unidentified proteins. Similar considerations pertain to the use of albumin, a major plasma protein in conventional serum-free media. [See Yamane et al., *Proc. Japan Acad.*, 57B(10):385-389 (1981) wherein it is stated at page 388: "BSA is, needless to say, a serum protein which is often discrepant in its cell growth promoting action of each commercial preparation."] As it is difficult to purify albumin on a large scale, commercially available albumin preparations can contain other contamination proteins, and not even crystallized preparations exceed 98% purity. "In addition to contaminating proteins, albumin preparations can be presumed to contain other hydrophobic substances including fatty acids and steroid hormones, and traces of salts and buffers used in the purification along with their contaminating transition metal ions." Iscove, id. at page 176. Therefore, it would be advantageous to eliminate from cell culture media both serum and albumin, as well as other proteins as lipid carriers. This invention provides the option of eliminating such lipid carriers.

Attempts have been described in the literature to supply lipids as liposomes to cells in culture [N. N. Iscove, Culture of Lymphocytes and Hemopoietic Cells in Serum-Free Medium, p. 169-185, in D. W. Barnes, D. A. Sibasku, G. H. Sato (eds.), Methods for Serum-Free Culture of Neuronal and Lymphoid Cells, Alan R. Liss, NY (1984)], Poste, G. D. et al., *Methods in Cell Biology,* 14:43-71 (1976), D. M. Prescott, (ed.)], and M. Kriegler, *Cell,* 33(2):413-422 (1983). These liposomes are most typically prepared by sonicating the lipid mix in the presence of a protein (albumin) and result in particles of size typically about 25 nm [H. J. Morton; How to Prepare Media Containing Fat-Soluble Substances, Chapter 23, p. 353-357, in C. Waymouth, R. G. Ham, P. J. Chapple (eds.), The Growth Requirements of Vertebrate Cells *In Vitro*, Cambridge University Press, Cambridge, 1981.

Iscove, id. at page 179-181, provides an example of the prior art process used to supply lipids to serum-free culture. In such a process, lipids are mixed by being dissolved in chloroform; the chloroform is then evaporated and the lipids are "dried onto the bottom of the beaker." A suspending medium containing albumin is then added and the mixture is sonicated to disperse the lipids in the form of vesicles—liposomes small enough to pass through the pores of a sterilizing filter (0.45 μm). Iscove's following description of such a process points out some of the inherent problems of supplying lipids to culture medium in such a manner:

At the end of the sonication period, a few small aggregates of soybean lipid may have escaped dispersion. These are ignored. The suspension is passed once through a membrane of 1.2 μm pore size . . . after which it usually passes without difficulty through a sterilizing 0.45 μm filter. If the filter blocks rapidly, it may be helpful to pass the suspension once more through a 1.2 μm membrane. The grey residue on the filter is particulate metal shredded from the sonicator probe. Filtration is easiest immediately after sonication and should not be delayed . . . .

The resulting suspensions are stored at 4° C. They may become somewhat more opaque in the first day or two of storage. This change probably reflects some coalescence of the liposomes to larger average size but has no influence on their effectiveness in culture . . .

Because of quantitative variation in the completeness of dispersion and retention on the sterilizing filters, each individual lipid preparation should be titrated in culture to determine its optimal concentration . . . .

Filter-sterilization of medium which has already been supplemented with lipid should be avoided, since there is a risk of retaining an indeterminate amount of lipid on the filter. [Emphasis added.]

The introduction of lipids to cell culture media according to this invention enhances the availability of lipids to the cells and avoids globular lipid aggregates that can be lost in filtration and thus become unavailable to the cells. This invention further provides the option of not having to filter sterilize the lipid component and the rest of the media components separately.

SUMMARY OF THE INVENTION

This invention concerns stable lipid microemulsions which can be added to cell culture media to provide essential lipids in a bioavailable form. The invention further concerns cell culture media in which lipids are supplied in the form of such lipid microemulsions.

This invention further provides for methods to disperse lipids in culture media by the use of one or more emulsifiers. The emulsifiers are preferably phospholipids and/or non-toxic polymeric detergents, and still more preferably lecithin and/or Pluronic polyols and/or polysorbate compounds.

This invention further provides for a lipid solution component comprising lipids, an organic solvent and one or more emulsifiers, and an aqueous component comprising one or more emulsifiers and water. It is the addition with agitation as by vortexing of the aqueous component to the lipid solution component which results in the formation of a lipid microemulsion.

DETAILED DESCRIPTION

The introduction of lipids in the form of microemulsion enhances the availability of the lipids in the media to the cells. A microemulsion is herein defined as a preparation wherein one liquid is distributed in small globules throughout the body of a second liquid wherein said small globules are herein described as micelles. The globules may be of a continuous phase, or may be monolamellar or multilamellar vesicles. The lipid microemulsions of this invention are prepared by combining with agitation an aqueous component and a lipid solution component, wherein the aqueous component is herein defined as comprising one or more emulsifiers in water, and the lipid solution component is herein defined as comprising one or more lipids and one or more emulsifiers in an organic solvent.

As indicated above, the lipid microemulsions of this invention provide a means of eliminating lipid carriers such as serum, serum albumin, or other proteins from culture media. Within the scope of this invention are also media which correspond to conventional culture media except that the serum moiety is partially replaced with at least one lipid nutrient in the form of a microemulsion of this invention. Therefore, serum or other proteinaceous substances such as albumin of conventional media can be reduced or dispensed with according to this invention. Use of the culture media of this invention makes it easier to isolate and purify the product accumulated in the media. Mass production of culture media is also made easier, according to this invention.

Another advantage of this invention is that preferred emulsifiers of this invention, Pluronic polyols, are already used as physical protectants in mammalian cultures, and have been shown therein to be non-toxic to cells and non-inhibitory to cell growth. Kilburn et al., *Biotech. & Bioengin.*, Vol X:801-814 (1968); Mizrahi, *Develop. Biol. Standard*, 55:93-102 (1984); and Mizrahi, *J. Clin. Microbiol.*, 2(1):11-13 (July 1975). Copending, commonly owned U.S. Ser. No. 077,181 filed Jul. 24, 1987 and U.S. Ser. No. 077,303 filed Jul. 24, 1987, provide examples of successful cultivation of insect cells in media containing Pluronic polyols and the expression of recombinant proteins by such insect cells. U.S. Ser. No. 077,303 describes the use of lipid microemulsions herein disclosed in serum-free, low protein or essentially no protein media for insect cell culture. U.S. Ser. No. 077,181 discloses the successful culturing of insect cells in airlift fermentors.

Thus, Pluronic polyols, preferred emulsifiers of this invention, serve dual purpose in providing not only a physical protectant for agitated and/or sparged cultures but also in providing an emulsifying system for lipids to be supplied to the culture. Therefore, media of this invention provide an enhanced nutritional environment for the growth of cells under any culture conditions but especially for cells growth under agitated and/or sparged conditions, and, in general, for cultures that are well-aerated. As a consequence, the media thus provide an enhanced nutritional environment for the production of recombinant, viral and/or natural products, wherein examples of natural products are native proteins or monoclonal antibodies.

The term "protein" is herein defined to exclude the term "peptones." The media of this invention preferably contain very low concentrations of protein, that is, preferably less than about 1000 μg/ml, more preferably less than about 50 μg/ml, still more preferably less than about 10 μg/ml. If certain optional components are determined to be desirable as indicated below, for example, growth factors such as insulin, transferrin or catalase, they are present preferably at low concentrations and do not function as lipid carriers.

Lipids are defined herein as any of a heterogeneous group of fats and fatlike substances characterized by being water-insoluble and being extractable by nonpolor (or fat) solvents such as alcohol, ether, chloroform or benzene, among others. Lipids include unsaturated fatty acids, saturated fatty acids, steroids, lipid soluble vitamins and phospholipids and their esters. Examples of unsaturated fatty acids include linoleic acid, linolenic acid, oleic acid, arachidonic acid, and and their glycerides and esters. Preferred fatty acids also include fatty acid esters, preferably polyunsaturated fatty acid esters, and still more preferably, mixtures of polyunsaturated fatty acid methyl esters, as for example, those found in fish liver oil, preferably cod liver oil. Examples of saturated fatty acids include palmitic acid and stearic acid and their glycerides. Examples of lipid soluble vitamins include vitamins A, D and E. Examples of steroids, that is lipids which contain a hydrogenated cyclopentophenanthrene-ring system, include progesterone, adrenocortical hormones, the gonadal hormones, cardiac aglycones, bile acids and sterols (such as cholesterol). Preferred steroids are sterols, preferably cholesterol.

The type of lipids to be supplied to cell culture media of this invention depend on the choice of cells to be cultured. Also, lipids are supplied in concentrations appropriate for the particular cell line being cultured, wherein the concentration is not toxic to the cells and is non-inhibitory to cell growth. For example, insect cells appear to be able to tolerate a higher concentration of lipids than mammalian cells. Exemplary lipid components for a mammalian cell culture are shown in Examples 1 and 2, below whereas another exemplary lipid component of Example 1 for the mammalian cells is shown in Example 3. The lipid component of Example 1 for the mammalian cells is the same as that for the insect cells of Example 3 except in the respect that the concentrations of the lipid and the emulsifier Tween 80 are ten times less for the mammalian lipid component than for the insect lipid component. Preferred ranges for lipids for insect cells are as follows. A mixture of polyunsaturated fatty acid methyl esters, such as, fish liver oil, preferably cod liver oil, is preferably present in the media at a concentration of from about 1 mg/l to about 50 mg/l, preferably from about 5 mg/l to about 15 mg/l, and most preferably about 10 mg/l. Said concentrations of cod liver oil further contain the preferred concentrations of the lipid soluble vitamin A. The sterol, preferably cholesterol, is at a concentration from about 2 mg/l to about 7 mg/l, more preferably from about 3 mg/l to about 5 mg/l, and most preferably about 4.5 mg/l. The alphatocopherol of the lipid component is at a concentration of from about 0.5 mg/l to about 4 mg/l, more preferably about 2 mg/l.

Preferred examples of insect cell culture media containing the lipid microemulsions of this invention are those disclosed in claimed in U.S. Ser. No. 077,303. The compositions of three of such preferred serum-free, low protein or essentially no protein media for insect cell culture used in the examples below are outlined in Table 1. The Pluronic Polyol-Lipid Microemulsions in Table 1 are prepared according to Example 3, infra.

TABLE 1

Serum-Free Insect Media Containing Lipid Microemulsions

| | SFM2M With No Bovine Serum Albumin (BSA) | ISFM-3 | ISFM-4 |
|---|---|---|---|
| IPL/41 Basal Medium Ultrafiltered Peptones | Yes | Yes | Yes |
| Tryptose Phosphate Broth | 2.6 g/l | No | No |
| Bactocasitone (caseine digest) | 1 g/l | No | No |
| Panmede (ox liver digest) | 1 g/l | No | No |
| Yeastolate (yeast extract) | 1 g/l | 2 g/l | 4 g/l |
| Lactalbumin Hydrolyzate | No | 2 g/l | No |
| Extra Water Soluble Ingredients | | | |
| α-Glycerol phosphate | 1 g/l | No | No |
| Glycerol | 2 g/l | No | No |
| Folic Acid | 3.6 mg/l | No | No |
| Inositol | 10 mg/l | No | No |
| Catalase | 3 mg/l | No | No |
| Pluronic Polyol-Lipid Microemulsion | | | |
| Pluronic Polyol F68 in Water | 1 g/l | 1 g/l | 1 g/l |
| Cod Liver Oil | 10 mg/l | 10 mg/l | 10 mg/l |
| Tween 80 | 25 mg/l | 25 mg/l | 25 mg/l |
| Cholesterol | 4.5 mg/l | 4.5 mg/l | 4.5 mg/l |
| α-Tocopherol acetate | 2 mg/l | 2 mg/l | 2 mg/l |
| Ethanol | 1 ml/l | 1 ml/l | 1 ml/l |

An advantage of lipids being supplied in the form of a microemulsion, in addition to enhancing the availability of the lipids to the insect cells, is in providing the option of not having to filter sterilize the lipid fraction and the rest of the media components separately. The lipid microemulsions of this invention can be added to the media without being filter sterilized, and the entire media can then be filter sterilized without the concern of lipid loss during the filter sterilization process. For large-scale production, such an advantage is significant. However, it is of course possible to filter sterilize the lipid solution component and aqueous component separately and prepare the lipid microemulsion aseptically.

The lipid solution component of the media of this invention is prepared by combining the appropriate amount of a mixture of lipids, for example, a mixture of polyunsaturated fatty acids, alpha-tocopherol acetate and cholesterol, and the emulsifier(s), in an appropriate amount of an organic solvent, preferably a $C_1$-$C_3$ alcohol, more preferably ethanol, to form a solution. It is important that the final concentration of the organic solvent is non-toxic and non-inhibitory to cell growth. For example, a preferred concentration of ethanol as the organic solvent in preferred media of this invention would be approximately 1 ml/L. The lipid solution component is then optionally filter sterilized. (The lipid solution component can be stored under nitrogen in a temperature range of from about −20° C. to about −80° C.)

The aqueous component containing one or more emulsifiers, preferably protective agent/emulsifiers, is similarly optionally filter sterilized. The aqueous component, which is preferably of greater volume than the lipid solution component is slowly and, optionally aseptically, added to the lipid solution component with agitation as by vortexing. The lipid and aqueous components are preferably individually preheated to about 37° C. before being mixed. The lipid microemulsion is formed upon the addition with agitation of the aqueous component to the lipid solution component. (In general, it is preferred to add the aqueous component to the lipid solution component rather than vice versa.)

The optionally filter sterilized lipid microemulsion can then be added to the media. If the option of aseptically forming the lipid microemulsion from filter sterilized components is not taken, the option remains of filter sterilizing the entire medium after all additions are completed.

Emulsifiers preferred for preparing the lipid microemulsions of this invention are non-toxic polymeric detergents, bile salts, such as, deoxycholate, and/or phospholipids. Preferably, the emulsifiers are non-toxic polymeric detergents and/or phospholipids. It is further preferred that the non-toxic polymeric detergents are non-ionic and that the phospholipid emulsifier is lecithin. It is further preferred that there be one or more emulsifiers present in both the aqueous and lipid solution components.

Editions of McCutcheon's Emulsifiers & Detergents (published by the McCutcheon Division of MC Publishing Co., 175 Rock Road, Glenn Rock, N.J. U.S.A.) are examples of a source of finding non-toxic, non-ionic polymeric detergent candidates for use as emulsifiers of this invention. Infra, a simple test is outlined for selecting appropriate emulsifiers within the scope of this invention.

The emulsifiers are present at final concentrations in the media which are non-toxic to cells and noninhibitory to cell growth, reproduction and expression of products thereby. The emulsifiers are considerably more concentrated in the aqueous and lipid solution components than in the media in which they are diluted, preferably by a factor of 100 or 1000, respectively. For example, 10% Pluronic F68 in 10 ml of aqueous component and 25 mg of Tween 80 in 1 ml of lipid solution component once combined with agitation to form a lipid microemulsion which is then added to one liter of media are respectively diluted to concentrations of 0.1% (100 fold dilution for Pluronic F68) and to 25 mg/l (1000 fold dilution for Tween 80).

Very occasionally, the solubility limits of the volumes of the aqueous or lipid solution components could be reached before the maximum, non-toxic and beneficial concentration of a particular emulsifier has been reached for the medium as a whole. If such an event should occur, the emulsifier could be added directly to the medium, that is, outside of the lipid microemulsion, if it is determined that such an addition would be beneficial to the cells, as, for example, by enhancing the protective and/or emulsifying effects of a protective agent/emulsifier. Therefore, a preferred concentration (weight/volume) range for Pluronic polyols in the media of this invention would be from about 0.01% to about 1%; however, the solubility limit of Pluronic F68 is about 10% in water, and therefore, a 10 ml aqueous component would not be sufficient to accommodate the high end of the emulsifier concentration range in the final media. Additional Pluronic F68 could thus be added directly to the media if such additions would be considered necessary to optimize the protective/emulsifying effects of said protective agent/emulsifier. The concentration of Pluronic F68 in a 10 ml aqueous component would be preferably from about 1% to about 10%, more preferably from about 5% to about 10%, and still more preferably about 10%.

It is preferred that the emulsifiers of the aqueous component be protective agents. Protective agents are herein defined as non-toxic, water soluble compounds that functionally act to protect cells from damage and death in agitated and/or sparged cultures.

A protective agent candidate can be selected by first confirming that it is non-toxic to the cells to be cultured by methods known to those skilled in the an of cell culture, for example, by adding it to a suspension or monolayer of the cells of choice for cultivation and comparing the growth of the culture to a control. Then, the non-toxic protective agent candidates can be tested for protective ability by adding the candidate agent to an agitated and/or sparged culture of the cells of choice at small scale and observing viability and growth rate after an appropriate period and comparing the viability and growth rate of the cells of said culture to the viability and growth rate of the cells in a control culture. A source of finding non-toxic, non-ionic polymeric detergent protective agent/emulsifier candidates for the media of this invention can be found in Editions of McCutcheon's Emulsifiers & Detergents, supra.

It is further preferred that the emulsifier or emulsifiers of the aqueous component be block copolymers of propylene oxide and ethylene oxide (polyoxypropylene polyoxyethylene condensates). Preferably such protective agent/emulsifiers are Pluronic polyol, such as, Pluoronic F68, F77, F88 and F108, preferably F68 and F88, more preferably F68. The Pluronic polyols are commercially available from BASF Wyandotte Corp. (101 Cherry Hill Road, P.O. Box 181, Parsippany, N.J. 07054, U.S.A.).

The concentration of the protective agent/emulsifier(s) is preferably that which is most effective in protecting the cells from damage, but which concentration is non-inhibitory to cell growth, reproduction and expression of products thereby. The Pluronic polyol protective agent/emulsifiers are present in the media of this invention preferably at a concentration (weight/volume) of from about 0.01% to about 1%, more preferably from about 0.05% to about 0.5%, and most preferably about 0.1%.

However, it is not necessary for the emulsifier or emulsifiers of the aqueous component to be protective agents to practice this invention. Any non-toxic emulsifiers, that are non-inhibitory to cell growth, reproduction and expression of viral, recombinant or natural products, such as, antibodies or native proteins, can be used. Preferably, however, if the emulsifier or emulsifiers of the aqueous component are not protective agents, other protective agents would be included in the media if the culture is to be well-aerated. Such other protective agents would be preferably cell surface stabilizing agents and/or viscosifying agents and/or bubble surface tension reducing agents. Examples of preferred protective agents other than non-toxic polymeric detergents are hydroxyethyl starch, methyl cellulose, carboxymethyl cellulose (as, sodium carboxymethyl cellulose), dextran sulfate, polyvinylpyrrolidone, ficoll, alginic acid and polypropyleneglycol.

Preferred emulsifiers in the lipid solution component are phospholipids and non-toxic, non-ionic polymeric detergents. A preferred phospholipid emulsifier is lecithin and preferred non-toxic, non-ionic polymeric detergent emulsifiers are polysorbate compounds having the formula:

wherein R is a saturated or unsaturated fatty acid having from 16 to 20 carbons, inclusively;

wherein t is an integer between 10 and 30, inclusively; and wherein u is an integer between 10 and 20, inclusively.

Most preferably, such a polysorbate emulsifier is polyoxyethylene (20) sorbitan monooleate, otherwise known as polysorbate 80. Such a non-toxic, non-ionic polymeric detergent is commercially available as Tween 80 from ICI Americas Inc. (New Murphy Road & Concord Pike, Wilmington, Del. 19897, USA). Another polysorbate 80 is commercially available as Durfax 80 from Durkee Industrial Foods Group/SCM Corp. (900 Union Commerce Bldg., Cleveland, Ohio 44115, USA). Such a non-ionic, non-toxic, polymeric detergent/emulsifier, such as, polysorbate 80, is preferably present in the lipid solution components of this invention at a concentration from about 0.5 mg/ml to about 75 mg/ml, more preferably from about 1 mg/ml to about 30 mg/ml, and more preferably from about 2.5 mg/ml to about 25 mg/ml.

Optional ingredients that can be added to the lipid solution component include reducing agent/anti-oxidants, such as, dithiothreitol, β-mercaptoethanol and monothiolglycerol wherein monothiolglycerol is a preferred reducing agent/anti-oxidant. Such ingredients are considered amphipathic if they are soluble in both the aqueous and the lipid solution components, and are preferably added to the lipid solution component in appropriate concentrations for the chosen cell line.

Testing whether an emulsifier, a protective agent/emulsifier, combination of emulsifiers, or a combination of a protective agent/emulsifier and an emulsifier or emulsifiers is effective in emulsifying the lipids to be supplied to the media of this invention can be simply performed as follows. First, the candidate emulsifier or combination of emulsifiers must be confirmed as non-toxic to the cells of choice in a manner as described above for candidate protective agents. Secondly, the emulsifying ability of the candidate emulsifier(s) is tested at the determined non-toxic concentrations. The appropriate lipids are dissolved in an appropriate organic solvent, preferably an alcohol ($C_1$–$C_3$), more preferably ethanol. The candidate emulsifier or each of the combination of emulsifiers is then combined with the lipid solution or in the separate aqueous solution, depending upon in which solution, that is, the organic or aqueous, the candidate emulsifier is more readily combinable. Then the aqueous component is added to the lipid solution component and vigorously agitating as by vortexing and preferably at 37° C. A clear to slightly translucent microemulsion should form if the lipids are successfully emulsified.

For the candidate emulsifier selection test, at least one emulsifier should be present in the lipid solution component and one in the aqueous component. If only one candidate emulsifier is being tested, it can be tested with a known emulsifier, such as, for example, if the candidate emulsifier is readily combinable in water, it could be tested in a candidate aqueous component with Tween 80 as the emulsifier in the lipid solution component; whereas, if the candidate emulsifier is readily combinable in a solution of appropriate lipids, it could be tested with Pluronic F68 in an aqueous component. Another option would be to test a sole candidate emulsifier in both the aqueous and lipid solution components, that is, wherein the same emulsifier would be present at appropriate concentrations in both a candidate aqueous component and a candidate lipid solution component.

One option for emulsifying lipids to be supplied to cell culture media according to this invention is a dual emulsifier system wherein, as noted above, the protective agent is an emulsifier as well as a protective agent and can act in conjunction with an emulsifier or combination of emulsifiers present in the lipid solution component. A preferred example of a dual emulsifier system of the media of this invention is the combination of a protective agent/emulsifier, preferably a Pluronic polyol, more preferably Pluronic F68 or Pluronic F88, and still more preferably Pluronic F68, and a non-toxic non-ionic polymeric detergent, preferably a polysorbate compound, and more preferably polysorbate 80.

Another option for emulsifying lipids according to this invention is a system wherein the protective agent is not significantly emulsifying but wherein one or more additional emulsifiers are present in the aqueous component which is added to the lipid solution component and act in conjunction with the emulsifiers present therein to form a microemulsion.

The choice of media to which the lipid microemulsions of this invention are added depends on the particular cells that are being cultured. There are commercially available media for all cell types.

For example, there are a wide variety of commercially available media for insect cell culture which include such commercial available basal medium as, for example, TC10 without tryptose broth [commercially available from Microbiological Associates; see Gardiner et al., *J. Invert. Pathol.*, 25:363 (1975)], Grace's Antheraea medium [Vaughn et al., *TCA Manual*, 3(1) (1976); Yunker et al., *Science*, 155:1565–1566 (1967)], Medium M20 of Mark's [Vaughn et al., *TCA Manual*, 3(1) (1976); Marks, In Kruse et al. (eds), *Tissue Culture Methods and Applications*, pp. 153–156 (1973)], Goodwin's IPL-52 Medium [Goodwin, *In Vitro*, 11:369–378 (1975)], Goodwin's IPL Medium [Goodwin et al., In Kurstak et al. (eds.), *Invertebrate Systems In Vitro* (1980)], Goodwin's IPL-76 Peptone Medium [Goodwin et al., id.; Goodwin et al., *In vitro*, 14:485–494 (1978)], Hink's TMH FH Medium (Revised) [Hink, *Nature* (London), 226:466–467 (1970)], Medium S-301 of Hansen [Hansen, In Maramorosch (ed.), *Invertebrate Tissue Culture Research Applications*, pp. 75–99 (1976)]; Vaughn et al, *TCA Manual*, 3(1) (1976)], and IPL-41 Medium [Weiss et al., *In, Vitro*, 17(6):495–502 (1981)], wherein IPL-41 is a preferred basal medium.

IPL-41 basal medium is commercially available from a number of vendors (J. R. Scientific, Woodland, Calif.) and is described in Weiss et al., *In Vitro*, 17(6):495–502 (June 1981) and in Weiss et al., *CRC Press*, supra, pp. 70–72 (1986). Table 1 of Weiss et al. (*In Vitro*) at page 496, and Table 3 of Weiss et al., *CRC Press*, at pages 71–72 outline all the components of IPL-41 and provide their proportions in mg/l; said tables are herein incorporated by reference. At page 497 of Weiss et al., (*In Vitro*), the preparation of the complete medium IPL-41 is described wherein tryptose phosphate broth (TPB) and fetal bovine serum (FBS) are added. The IPL-41 basal medium employed in preparing the media of this invention preferably does not contain tryptose phosphate broth (TPB) or fetal bovine serum (FBS). Co-pending, commonly owned U.S. Ser. No. 077,303 describes preferred replacements for serum and tryptose phosphate broth wherein lipid microemulsions of this invention supply the lipid fraction in insect culture media.

A "basal medium" is herein defined as a nutrient mixture of inorganic salts, sugars, amino acids, optionally also containing vitamins, organic acids and/or buffers. Basal media together with supplements provide the nutrients necessary to support cell life, growth and reproduction. The choice of basal media used as the starting point for preparing the media of this invention is not critical, but should be appropriate for the cell line selected and would most preferably contain little or no serum, serum albumin or other lipid carders. The basal medium can also be considered optional in the sense that appropriate peptone and lipid components can be selected which provide such necessary nutrients as amino acids and vitamins required to support cell life, growth, reproduction, and expression of recombinant or viral products and production of antibodies.

Commercially available media for mammalian cells include Dulbecco's Modified Eagle Medium (S-DME; available from Irvine Scientific, Santa Ana, Calif. USA); RPMI 1640 Medium (also available from Irvine Scientific); HL-1 (Ventrex Labs, Portland, Me. USA); HB 104 (Hana Biologicals, Berkeley, Calif. USA); Eagle Minimum Essential Medium; and Ham F-12 Medium; RITC 80-7 [Yamane et al., *Exp. Cell. Res.*, 134:470 (1981)]; RITC 56-1 [Yamane et al., In Kohno et al. (eds.), *International Symposium on Clinical Potentials and Interferons in Viral Disease and Malignant Tumors*, pp. 355–364.

Examples of media for plant cell culture include those described in Murashige et al., *Physiol. Plant*, 15:473 (1962); Gamborg et al., *Exp. Cell. Res.*, 50:151 (1968); and Gamborg et at., *In Vitro*, 12:473 (1976).

Further examples of culture media for animal cells, algae, bacteria, fungi and protozoa can be found in Cote et al. (eds.), *ATCC Media Handbook*, first edition 1984 (ATCC 1984).

The media of this invention can also include other preferably water-soluble ingredients, for example, insulin to enhance glucose uptake, transferrin for iron transport, trace elements as selenium, catalase as a peroxidation protectant, ethanolamine as a lipid precursor, steroid hormones as testosterone, thyroid hormone as triiodothyronine, nucleic acid precursors such as hypoxanthine, thymidine, deoxyadenosine, and deoxycytidine, as well as vitamins, minerals, amino acids and other nutrients such as L-glutamine, pyruvate, alpha-glycerol phosphate, glycerol, folic acid, and inositol which are contained in conventional serum-supplemented or serum free media for cell culture. Although some of such ingredients are proteins, they are not being supplied for the purpose of carrying lipids and are preferably at low concentrations.

The method of preparing a culture medium to which the lipid microemulsions of this invention are added is not critical. The media may be prepared, for example, by dissolving all the ingredients and additives in water in their respective appropriate concentrations first and then filtering the solution on a membrane filter under pressure to get a sterilized culture medium.

The method of culturing cells with the media of this invention is also not critical. Cells are cultured in the media of this invention under approximately the same conditions as those for conventional culture media, except that whenever possible, cells should be grown under well-aerated conditions, that is, in agitated and/or sparged cultures. For optimal culture conditions for the growth of insect cells see U.S. Ser. Nos. 077,181 and 077,303 which are herein incorporated by reference.

In general, insect cells grown in the media of this invention are cultured in a temperature range and under conditions appropriate for the particular cell line selected. For example, *Spodoptera frugiperda* cells, preferably Sf9 cells, are cultured in a temperature range of from about 25° C. to about 28° C. and wherein the pH of the culture medium is preferably maintained in a range from about 6 to about 7, more preferably about 6.2 to about 6.4.

The media of this invention are employable not only for the growth of cells, but also for the production of useful physiologically active substances such as interferons, lymphokines and antibodies. According to the examples of this invention, recombinant CSF-1 is produced by host insect cells cultured in media containing lipid microemulsions of this invention. "Colony stimulating factor (CSF-1)" refers to a protein which exhibits the spectrum of activity understood in the art for CSF-1, that is, when applied to the standard in vitro colony stimulating assay of Metcalf, *J. Cell Physiol.*, 76:89 (1970), it results in the formation of primarily macrophage colonies. Native CSF-1 is a glycosylated dimer, dimerization may be necessary for activity. The term CSF-1 herein refers to both dimeric and monomeric forms.

Other heterologous proteins that have been expressed in insect cells via a baculovirus expression vector system (BEVS) are outlined in Summers et al., *Banbury Report: Genetically Altered Viruses in the Environment*, 22:319-329 (1985). However, those skilled in the an who have the benefit of this disclosure, will recognize that many other recombinant proteins can be produced by animal, plant and/or microbial cells according to this invention. Exemplary recombinant proteins include, without limitation colony stimulating factors [for example, long and short form CSF-1 or M-CSF, 6-CSF, GM-CSF and interleukin-3 among others], modified pro-urokinase or urokinase, tissue plasminogen activator (TPA), TPA-urokinase hybrids, toxic proteins such as whole ricin toxin, ricin A chain, products containing ricin A, as well as, interferons $\alpha,\beta$ and $\gamma$ and hybrids thereof), interleukins, tumor necrosis factor, erythropoietin and other hematopoietic growth factors, human growth hormone, as well as porcine, bovine and other growth hormones, epidermal growth factor, insulin, hepatitis B vaccine, superoxide dismutase, Factor VIII, Factor VIII C, atrial natriuretic factor, feline leukemia virus vaccines, as, for example, gp70 polypeptides, the light and heavy chains of antibody molecules, lectins such as *Ricin communis* agglutinin (RCA), diphtheria toxin, gelonin, exotoxin from *Pseudomonas aeruginosa*, toxic proteins from *Phytolacca americana* (PAPI, PAPII and PAP-s), insecticidal proteins from *Bacillus thuringiensis*, many enzymes as for example, CAT, as well as innumerable other hybrid proteins.

Further, as indicated above, a variety of monoclonal antibodies can be produced by hybridomas cultured in media of this invention and various viral products can be produced from insect cells so cultured.

Primarily, the media of this invention would be used for suspension cultures including microcarrier cultures. The lipid microemulsions of this invention can however be added to any media to which lipids are considered a beneficial addition. In general, if cells can be grown successfully in media wherein serum, albumin, other proteinaceous lipid carrier or other non-protein lipid carriers, such as a cyclodextrin or mixture of cyclodextrins (see Yamane et al., supra; U.S. Pat. No. 4,533,637), are employed, then the cells can be grown in the media of this invention wherein the lipids are supplied as a lipid microemulsion and other required hormones and growth factors are required.

The reason lipids are supplied to the cells is not critical. They can be supplied as a microemulsion according to this invention whether they are considered as essential or growth promoting nutrients, physical or chemical protectants or as having other functions, as for example, as a solvolytic agent, as a membrane modifying agent, as a surface tension reducing agent and/or as a cell surface stabilizing agent.

The cells can be of animal, microbial or plant origin. If animal cells, they can be from vertebrates or invertebrates. Preferably, the cells are those which can produce recombinant, viral and/or natural products. Exemplary vertebrate cells are mammalian cells, for example, lymphocytes, fibroblasts, epithelial cells, ovarian cells, and their transformed cells, various neoplastic cells, and hybridomas derived therefrom. More specifically, examples of mammalian cells include Chinese Hamster Ovarian cells, Epstein-Barr Virus (EBV)-transformed human lymphoblastoid cell lines such as UMCL and C51804, human Burkitt's lymphoma-derived Namalwa cells, murine lymphoid cell-derived myeloma SPI cells, human fibroblast cells such as HEL and IMR-90, human tumor-derived epithelial cells such as HeLa-$S_3$, Hep-2 and KB, human primary cultured cells, rat Yoshida sarcoma cells, hamster fibroblast cells BHK-21, murine fibroblast cells 3T3, murine lymphoma cells YAC-1, human/mouse hybridomas such as stable cell line D-234-4-27-8 which produces anti-LPS IgM (deposited at the American Type Culture Collection, Rockville, Md. USA on Aug. 10, 1984 under ATCC Accession No. HB 8598) and hybridomas which produce monoclonal antibodies to human fibroblast interferon as described in copending, commonly owned U.S. Ser. No. 325,969 (Erlich et al.) filed Nov. 30, 1981.

Exemplary invertebrate cells are insect cells, preferably cells which can produce viral or recombinant products upon infection, respectively, with either wild-type viruses or recombinant baculoviruses and which have been shown to grow, reproduce and express recombinant and/or viral products in a medium containing serum, albumin, another protein and/or other lipid carriers. For example, insect cells that can be grown in IPL-41 basal medium containing approximately 10% serum, can be grown in media wherein lipids are supplied as microemulsions according to this invention. Such insect cell lines include *Bombyx mori, Lymantria dispar, Trichoplusia ni* and *Spodoptera frugiperda*. [See generally, Granados et al. (eds.), *The Biology of Baculoviruses* (CRC Press 1986); Vaughn, *Adv. Cell. Cult.*, Maramorosch (ed.), *Invert. Tissue Culture: Research Applics.*, p. 295 (1976); and Vaughn, In, Barigozzi (eds.) *Proceedings of Internatl. Colloq. Invert. Tissue Culture*, (2nd, Tremezzo, 1967), p. 119 (1968).]

Further, insect cells that can be grown in the media of this invention are preferably from any order of the Class Insecta which can be hosts to a baculovirus expression vector system, or other wild-type viruses, but are preferably frown the Diptera or Lepidoptera orders. About 300 insect species have been reported to have nuclear polyhidrosis virus (NPV) diseases, the majority (243) of which were isolated from Lepidoptera. [Weiss et al., "Cell Culture Methods for Large-Scale Propagation of Baculoviruses," In Granados et al. (eds.), *The Biology of Baculoviruses*: Vol. II Practical Application for Insect Control, pp.63–87 at p. 64 (1986).] Insect cell lines derived from the following insects are exemplary: *Carpocapsa pomonella* preferably cell line CP-128); *Trichoplusia ni* (preferably cell line TN-368); *Autographa californica; Spodoptera frugiperda* (preferably cell line Sf9); *Lymantria dispar; Mamestra brassicae; Aedes albopictus; Orgyia pseudotsugata; Neodiprion sertifer; Aedes aegypti; Antheraea eucalypti; Gnorimoschema opercullela; Galleria mellonella; Spodoptera littolaris; Blatella germanica; Drosophila melanogaster; Heliothis zea; Spodoptera exigua; Rachiplusia ou; Plodia interpunctella; Amsaeta moorei; Agrotis c-nitrum, Adoxophyes orana, Agrotis segetum, Bombyx mori, Hyponomeuta malinellus, Colias eurytheme, AntiCarsia germmetalia, Apanteles melanoscelus, Arctia caja,* and *Porthetria dispar*. Preferred insect cells are from *Spodoptera frugiperda*, and especially preferred is cell line Sf9. The Sf9 cell line used in the examples herein was obtained from Max D. Summers (Texas A & M University, College Station, Tex. 77843 USA). Other *S. frugiperda* cell lines, such as IPL-Sf21AE III, are described in Vaughn et al., *In Vitro*, 13:213–217 (1977).

The preferred insect cell lines cultured in the media of this invention are suitable for the reproduction of numerous insect-pathogenic viruses such as parvoviruses, pox viruses, baculoviruses and rhabdoviruses, of which nucleopolyhidrosis viruses (NPV) and granulosis viruses (GV) from the group of baculoviruses are preferred. Further preferred are NPV viruses such as those from Autographa spp., Spodoptera spp., Trichoplusia spp., Rachiplusia spp., Galleria spp. and Lymantria spp. More preferred are baculoviruses strains *Autographa californica* NPV (AcNPV), *Rachiplusia ou* NPV, *Galleria mellonella* NPV and any plaque-purified strains of AcNPV, such as E2, R9, S1, M3, characterized and described by Smith et al., *J. Virol.*, 30:828–838 (1979); Smith et al., *J. Virol.*, 33:311–319 (1980); and Smith et al., *Virol.*, 89:517–527 (1978).

European Patent Application 127,839 (published Dec. 12, 1984) to Smith et al. describes a method for producing a recombinant baculovirus expression vector, capable of expressing a selected gene in a host insect cell. Said European application is herein incorporated by reference. The recombinant baculovirus expression vector is cotransfected with wild-type baculovirus DNA into a host insect cell, wherein recombination occurs. Recombinant baculoviruses are then detected and isolated according to methods described in EP 127,839 and Summers et al., "A Manual and Methods for Baculovirus Vectors and Insect Cell Culture Procedures," Texas Agricultural Experiment Bulletin No. 1555 (Texas A & M University; May 1987). The resultant recombinant baculovirus is then used to infect cultured insect cells and the protein product from the incorporated selected gene is expressed by the insect cells and secreted into the medium. Exemplified therein is the production of recombinant $\beta$-interferon, interleukin-2, and chloramphenicol acetyltransferase (CAT) via the culturing of *S. frugiperda* cells infected with a recombinant AcNPV expression vector into the genome of which the appropriate gene had been inserted. Further information concerning such a recombinant baculovirus expression system and its use in expressing recombinant proteins can be found in Summers et al., id.

Copending, commonly owned U.S. Ser. Nos. 077,188, 077,586 and 077,126 describe, respectively, the expression at high levels of biologically active recombinant colony stimulating factors, modified pro-urokinase, urokinase and novel hybrid proteins thereof, and ricin toxin proteins, wherein an insect cell/baculovirus expression system is employed to produce such proteins.

U.S. Ser. No. 077,188 specifically describes the construction of baculovirus CSF-1 expression and transfer vectors, including pAcM4 and pAcM6, used to prepare the recombinant baculoviruses AcM4 and pAcM6 by cotransfection with baculovirus DNA in Sf9 cells. Said recombinant baculovirus transfer vectors pAcM4 and pAcM6 referred to in the examples below has been deposited at the American Type Culture Collection (ATCC) [12301 Parklawn Drive, Rockville, Md. 20852 (USA)] on Jun. 12, 1987 in *E. coli*/MM294 under the respective designations ATCC Nos. 67429 and 67438. Said vectors have also been deposited and are maintained in the Cetus Master Culture Collection (CMCC) under the respective designations CMCC No. 3002 and CMCC No. 2996. Recombinant baculovirus AcM4 carries a nucleotide sequence which encodes for a 150 amino acid form of rCSF-1 whereas the recombinant baculovirus AcM6 carries a nucleotide sequence which encodes for a 522 amino acid form of rCSF-1.

The effect of timing of the infection of the insect cells with a recombinant baculovirus has been shown to be critical for enhanced specific productivity. The specific production of the recombinant protein was found to be constant during the exponential phase of cell growth under non-oxygen limited conditions. Late infection, under non-exponential growth conditions, resulted in lower specific productivity and lower final titer. It is preferred that the exponential growth phase be extended to the highest possible cell densities to achieve the highest total productivity of the recombinant protein product. Infection of the host insect cells under conditions that limit growth, for example, in the stationary phase of cell growth, results in a reduced specific productivity of the recombinant protein product.

Specific productivity (U or mg/cell) of the recombinant protein product is relative independent of cell density at the time of infection as long as the culture is in exponential growth. For example, when *Spodoptera frugiperda* cells are the host insect cells and when preferred media of this invention as described for insect cells in U.S. Ser. No. 077,303, are used, cell densities of from about $1.0 \times 10^6$ to about $4.0 \times 10^6$ cells/ml are preferred for infection with the recombinant baculovirus, more preferably from about 2.5 to about $3.5 \times 10^6$ cells/ml.

When employing the baculovirus expression vector system, the timing of the harvest of the recombinant protein product is critical to avoid contamination of the recombinant protein by viral and cell lysis proteins and to simplify thereby the downstream purification of the recombinant protein. With considerations for the stability of the product, it would be preferred to harvest the recombinant product before significant cell lysis has occurred.

Further, each recombinant, viral or native product expressed in the media of this invention should be checked for stability and degradation over the course of the fermentation run. Such considerations should enter into a determination of the optimal harvest time.

The following examples further illustrate the aqueous and lipid solution components, the lipid microemulsions, media and methods of this invention. These examples are not intended to limit the invention in any manner.

EXAMPLE 1

Lipid Microemulsion Preparation for Mammalian Cells 10 mg of cod liver oil, 4.5 mg of cholesterol, 2.0 mg of alpha-tocopherol acetate and 25 mg of Tween 80 were added to 10 ml of ethanol, dissolved therein, and the solution was filter sterilized. To prepare a quantity of lipid microemulsion sufficient for approximately one liter of mammalian culture medium, 10 ml of 10% Pluronic F68 in water was slowly and aseptically added with agitation by vortexing to 1 ml of the lipid solution component. A microemulsion was thereby formed which can then be added to a culture medium that has already been filter sterilized.

EXAMPLE 2

Lipid Microemulsion Preparation for Mammalian Cells 10 mg of monothiolglycerol, 10 mg of linoleic acid, 10 mg of lecithin, 5 mg of cholesterol, 5 mg of alpha-tocopherol acetate, and 20 mg of Tween 80 were added to 10 ml of ethanol and dissolved therein. To prepare a quantity of lipid microemulsion sufficient for approximately 1 liter of mammalian culture medium, 10 ml of 10% Pluronic F68 in water was slowly added with agitation by vortexing to 1 ml of the lipid solution component. A lipid microemulsion was thereby formed which can be then added to a culture medium which medium can then be filter sterilized without a concern of loss of lipids during the process. This emulsion is referred to as the A7 emulsion.

EXAMPLE 3

Lipid Microemulsion Preparation for Insect Cells 100 mg of cod liver oil, 250 mg of Tween 80, 45 mg of cholesterol and 20 mg of alpha-tocopherol acetate were added to 10 ml of ethanol and dissolved therein. The lipid solution component was then filter sterilized.

To prepare a quantity of lipid microemulsion sufficient for about 1 liter of insect culture medium, 10 ml of 10% Pluronic F68 was slowly and aseptically added with agitation by vortexing to 1 ml of the lipid solution component. A microemulsion was thereby formed which can then be added to a insect cell culture medium that has already been filter sterilized.

EXAMPLE 4

Insect Cell Growth in Serum-Free Media Containing Lipid Microemulsion 50 ml cultures of Sf9 cells were grown in 250 ml shake flasks agitated at 100–150 rpm (wit an orbital radius of one-half inch) at 27° C., in both ISFM-3 and ISFM-4 media (Table 1) for a number of passages. Said media contain the lipid microemulsion described above in Example 3. Initially, the ISFM-4 culture had a longer lag phase than the ISFM-3 culture, but by the third passage, both cultures grew equally well with short lag phases. Both ISFM-3 and ISFM-4 cultures have longer lag phases than conventional serum containing insect culture media. The average growth characteristics of eight passages in both media are shown in Table 2 below. These media provide growth rates (Td=17–24 hours) maximum cell densities of about $5 \times 10^6$ cells/ml and cell viabilities (99–100%) which are comparable to those found in 10% serum containing media under similar culture conditions.

TABLE 2

| Lag Phase* (hours) | Population Doubling Time (hours) | Maximum Cell Density ($10^6$ cells/ml) |
|---|---|---|
| ISFM-3  14 | 22 | 5.0 |
| ISFM-4  15 | 22 | 6.1 |

*Lag phase was calculated by extrapolating the exponential phase plot (semi-log) back to the initial cell density (1 × $10^5$ cells/ml. The x-intercept hours of culture incubation) is equal to the lag phase.

Figure 1:
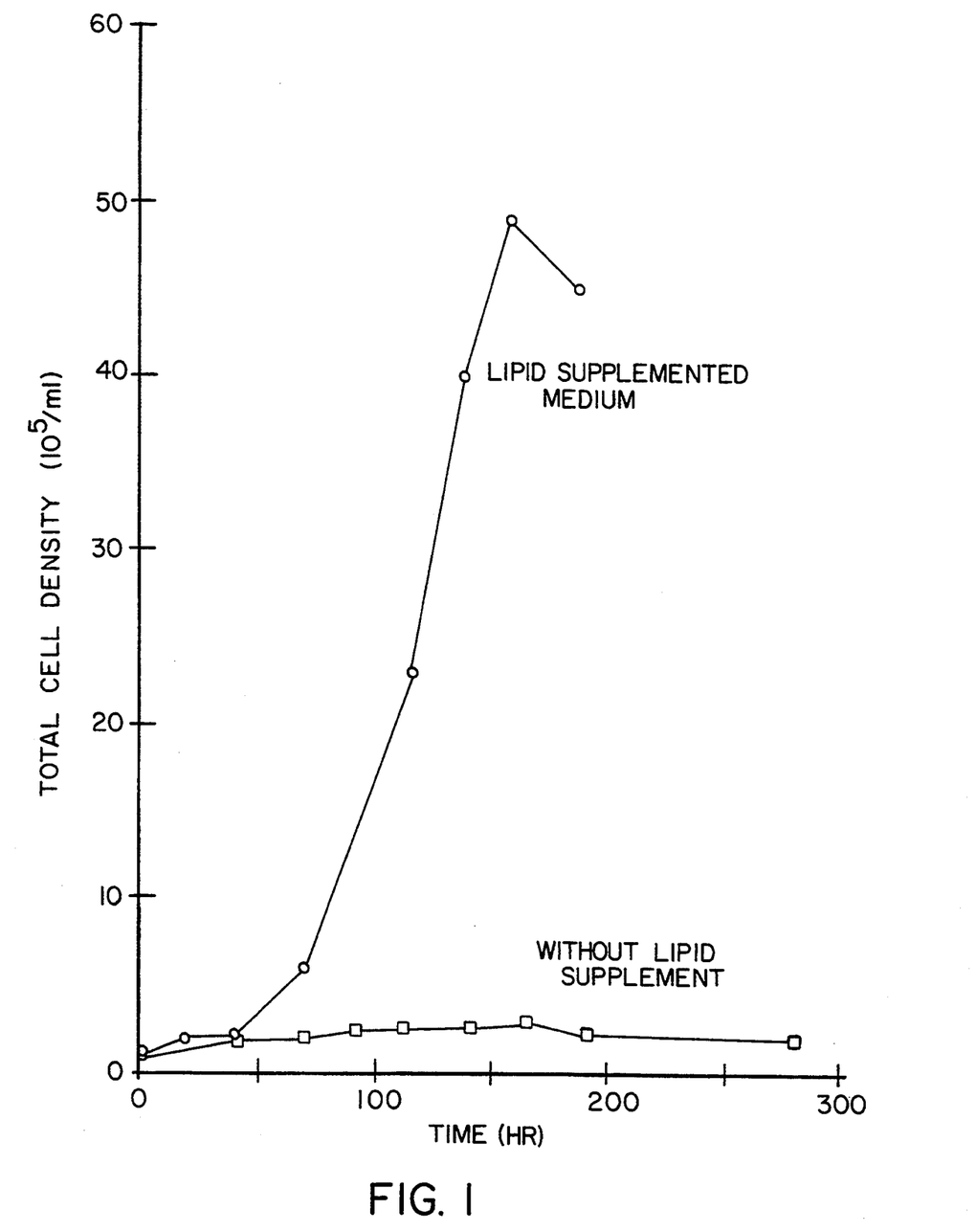
FIG. 1 shows the growth of Sf9 cells in the presence or absence of lipid supplement.

A second experiment was conducted to show the effect of the lipid supplement on the growth of Sf9 cells in ISFM-4 serum free media. After two passages in serum free media, the cells were seeded in serum free media with or without the lipid microemulsion of Example 3, and cell growth monitored. It is apparent from FIG. 1 that the microemulsion is required for Sf9 cell growth.

EXAMPLE 5

Production of Recombinant CSF-1 by Insect Cells Grown in Serum-Free Media Containing Lipid Microemulsion Sf9 cells grown for 25–30 passages (75–120 generations) according to the methods described in Example 4, above, were tested for production of rCSF-1 via a baculovirus expression vector system. A Sf9 culture in IPL-41 complete medium with tryptose phosphate broth (2.6 g/l) and 10% fetal bovine serum was employed as a control. An additional medium to those used in Example 4, that is, SFM2M without BSA as described in the Detailed Description above (Table I) was also used in this example.

The recombinant baculovirus AcM4 was used to infect exponentially growing cultures at a multiplicity of infection of 1. As shown in Table 3, below, the serum containing culture and the serum free cultures which contain lipid microemulsions of this invention produced similar levels of rCSF-1 (about $10^6$ U/ml) as measured by RIA.

TABLE 3 rCSF-1 Production by Sf9 Cells Growing in Various Media at 5 Days After Infection with AcM4

| Media | Cell Density at Infection ($10^6$ cells/ml) | rCSF-1 Produced by 5 Days Postinfection ($10^5$ RIA U/ml) |
|---|---|---|
| 10% Serum* | 3.2 | 9.1 |
| SFM2M without BSA | 2.5 | 10.2 |
| ISFM-3 | 3.1 | 10.1 |
| ISFM-4 | 3.0 | 9.9 |

*10% serum is IPL-41 complete medium with TPB and FBS.

EXAMPLE 6

Insect Cells Adapt Readily From Serum Containing Media to Serum Free Media Containing Lipid Microemulsion Sf9 cells maintained in 10% serum containing medium, that is, IPL-41 complete medium, readily adapted to SFM2M without BSA, ISFM-3 and ISFM-4 upon the first and second passages. Subsequent passages and infections with the recombinant baculovirus AcM4 and a second recombinant baculovirus AcM6 have confirmed that such media containing lipid microemulsions are suitable media for the large-scale growth of insect cells and for the production of recombinant protein products via a recombinant baculovirus expression vector system.

EXAMPLE 7

Growth of CHO Cells

The lipid microemulsions can be formulated in a wide variety of media, and are not restricted to insect cell media nor to culture of insect cells. CHO cells transformed with the M-CSF expression vector CHO/17/150, described in U.S. patent Ser. No. 243,253 filed Sep. 14, 1988 were seeded at an initial density of $1 \times 10^5$ and grown for 14 days, after which the media was assayed using standard radioimmune assay procedures. The lipid microemulsion shown in Example 1 was used to supplement media consisting of a 1:1 mixture of MCDB 301, described by Hamilton and Ham, in *In Vitro* 13:(9) 537, 1977; and DME-spinners, plus 4 mM glutamine, 10 μg/ml insulin, 10 μg/ml transferrin, 10 mg/ml ethanolamine, and 400 μg/ml lipid-free bovine serum albumin. Cells were grown both in serum free media, or media supplement with 1% fetal bovine serum. Table 4 shows that in serum containing media, CHO cells attain a density of about $1.3 \times 10^6$ cells/ml, and expreses m-CSF at a level of about 310,000 U/ml. In serum free media, a cell density of about $0.9 \times 10^6$ cells/ml is reached, and CHO cells in this media express about 240,000 U/ml of m-CSF.

TABLE 4

| Cell Line | Product | Serum-Supplemented | | | Serum-Free + Lipid Emulsion | | |
|---|---|---|---|---|---|---|---|
| | | Cell Density ($\times 10^6$/ml) | Product Level | Medium | Cell Density ($\times 10^6$/ml) | Product Level (mg/l) | Medium |
| Sf9 | Recombinant Hu M-CSF | 5 | 37 mg/l | ISFM4 + 10% FBS | 5 | 40 mg/l | ISFM4 |
| CHO | Recombinant Hu M-CSF | 1.3 | 310,000 /ml | BMCHO + 10% FBS | 0.9 | 240,000 /ml | BMCHO |
| NAMALWA | — | 6.8 | — | DM8 + 20% IPL/41 + 10% FBS | 3.7 | — | DM8 + 20% IPL/41 |
| MOPC21 Mu MYELOMA | Mu IgG | nd | nd | — | 3 | 100 mg/l | DM8 + 20% IPL/41 |

ISFM4: IPL/41, 4 g/l yeastolate, insect lipids.
BMCHO: 1:1 mix MCDB301 and DME-Spinners, 4 mM glutamine, 10 ug/ml insulin, 10 ug/ml transferrin, 10 mg/ml, ethanolamine, 400 mg/ml BSA, insect lipid mix (1/10 concentration).
DM8 + 20% IPL/41: sDME-HP, RPMI 1640 and IPL/41 (4:4:2). Also 5 ug/ml insulin, 5 ug/ml transferrin, 5 ng/ml selenium, 8 mM glutamine, 10 mg/ml ethanolamine and A7 lipids.

EXAMPLE 8

To further establish that the lipid microemulsions shown herein support the growth and product expression of other mammalian cell types, several cell lines of immunologic origin were cultured. Table 4 shows that the cell lines MOPC21 and Namalwa respond favorably to media supplement with the lipid microemulsion of Example 2.

The medium consisted of sDME-HP, RPMI 1640, and IPL/41 (4:4:2) supplemented with the microemulsion of Example 2. Also added were insulin (5 μg/ml), transferrin (5 ng/ml), selenium (5 μg/ml), glutamine (8 mM), and 10 mg/ml ethanolamine. An ELISA assay to determine antibody levels was run.

EXAMPLE 9

Characterization of Lipid Microemulsion Particle Size Before and After Sterile Filtration One of the advantages of the instant lipid microemulsions is that they are filter sterilizable alone or when combined with media. This is not true of prior art lipid compositions which are not readily filter sterilized with culture media because an indeterminate amount of lipid is not filtered, and remains trapped on the filter. Thus experiments were done to determine the particle size properties of the microemulsions which favor their filtration.

Figure 2:
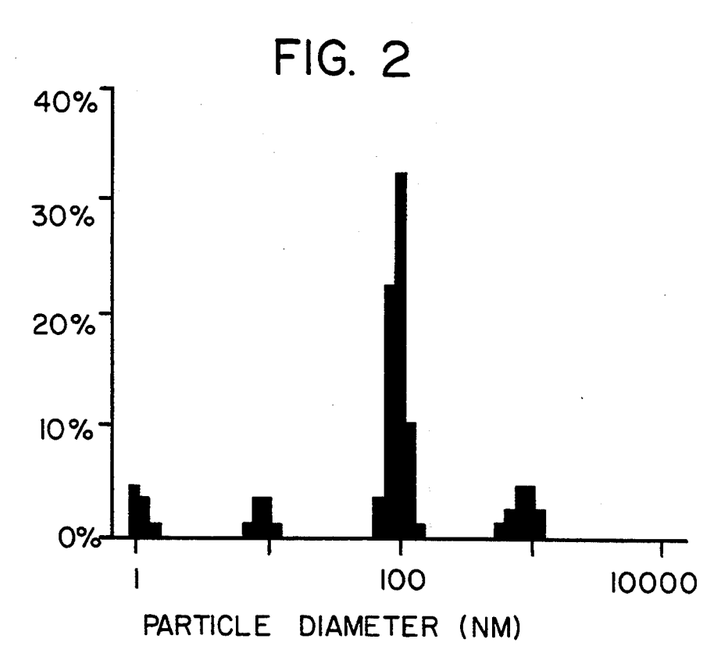
FIG. 2 shows the particle size diameter profile of an example lipid emulsion.

Differential laser light scattering measurements were made using a Coulter model N4M laster light scattering instrument and version 10.0W software. The lipid emulsion of Example 2 was prepared using standard procedures and was then diluted (1:5) in cell culture medium of Example 8 (dilution to this concentration was required to be in the range appropriate for the sensitivity of the instrument). Measuring intensity at a scattering angle of 90°, a major peak corresponding to particles of size about 95 nm was identified, with less intense peaks at about 9 and 890 nm (FIG. 2). The lipid mix was then filter sterilized through a 0.45 um filter (Sybron Nalge, Rochester N.Y., No. 120-0045) and the measurement repeated. Peaks corresponding to similar particle sizes (78, 6 and 860 nm) were again detected. Because one does not expect lipids with the particle size distribution observed, particularly those over 800 nm, to readily falter through an 0.45 μM filter, it is thought that the microemulsion distributes on filtration into smaller particles which are filterable and then reassociate.

Similarly, the particle size distribution was determined for the lipid mix of Example 3. The emulsion was prepared using standard methods and was then diluted (1:50) in IPL/41 medium and filter sterilized through a 0.45 μm filter. Measuring scatter intensity at a scatter angle of 30 degrees, a major peak was detected corresponding to particles of size about 280 nm, with less intense peaks detected at 25 and 1780 nm.

DEPOSIT

As mentioned above, the recombinant baculovirus transfer vectors pAcM4 and pAcM6 in *E. coli*/MM294 have been deposited at the American Type Culture Collection (ATCC), 12001 Parklawn Drive, Rockville, Md. 20852 (USA) on Jun. 12, 1987 under the respective ATCC Nos. 67429 and 67428. Further, the hybridoma cell line D-234-4-27-8 was deposited at the ATCC on Aug. 10, 1984 under Accession No. HB 8598.

Said deposits were made pursuant to a contract between the ATCC and the assignee of this patent application. The contract with the ATCC provides for permanent availability of said strains and progeny thereof upon issuance of a U.S. patent related to this application describing and identifying the deposits or upon the publication or laying open to the public of any U.S. or foreign patent application, whichever comes first, and for the availability of the strains and the progeny thereof to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the strains on deposit should die or be lost or destroyed when cultivated under suitable conditions, they will be promptly replaced upon notification with a viable culture of the same strain.

The deposits under the terms of the Budapest Treaty assure that said cultures deposited will be maintained in a viable and uncontaminated condition for a period of at least five years after the most recent request for the furnishing of a sample of the deposited microorganism was received by the ATCC and, in any case, for a period of at least 30 years after the date of the deposit.

Availability of the deposited swains is not to be construed as a license to practice the invention in contravention of the rights granted under the authority of any government in accordance with its patent laws.

Also, the present invention is not to be considered limited in scope by the deposited recombinant transfer vectors, since the deposited vectors are intended only to be illustrative of particular aspects of the invention. Any recombinant baculoviruses which can function to infect a host insect cell to produce a recombinant protein product is considered to be within the scope of this invention. Further, various modifications of the invention in addition to those shown and described herein apparent to those skilled in the art from the preceding description are considered to fall within the scope of the appended claims.

What is claimed is:

1. A lipid microemulsion free from serum albumin and prepared by combining at a temperature below the boiling point and with agitation, 10 ml of an aqueous component comprising one or more first emulsifiers at a concentration from 1% to 10% weight/volume and a preformed lipid component comprising one or more lipids and one or more second emulsifiers in an amount from 0.5 mg to 75 mg in 1 ml of a liquid organic solvent, wherein said lipid components remain as a stable emulsion in the aqueous component and said emulsion is non-toxic to cells in culture when added to a culture medium.

2. A lipid microemulsion according to claim 1, wherein the lipids in the lipid component are selected from the group consisting of unsaturated fatty acids, mixtures of polyunsaturated fatty acids, mixtures of polyunsaturated fatty acid methyl esters, lipid soluble vitamins and sterols, wherein the organic solvent is a $C_1$–$C_3$ alcohol and wherein the first emulsifier or emulsifiers are selected from the group consisting of pluronic polyols and the second emulsifier or emulsifiers are selected from the group consisting of phospholipids and nonionic, nontoxic polymeric detergents.

3. A lipid microemulsion according to claim 2, wherein the lipids are selected from the group consisting of linoleic acid; linolenic acid; oleic acid; fish liver oil; vitamins A, B, and E; and cholesterol;
   wherein the organic solvent is ethanol; and
   wherein the second emulsifier or emulsifiers are selected from the group consisting of lecithin and polysorbate compounds.

4. A lipid microemulsion according to claim 3 further comprising a reducing agent/anti-oxidant.

5. A lipid microemulsion according to claim 4 wherein the reducing agent/anti-oxidant is monothiolglycerol.

6. A lipid microemulsion according to claim 2 which is stored under nitrogen at a temperature range of from about −20° C. to about −80° C.

7. A lipid microemulsion according to claim 2 wherein said microemulsion comprises three subcomponents having particle diameters of about 6, 78 and 860 nm.

8. A lipid microemulsion according to claim 2 wherein said microemulsion comprises three subcomponents having particle diameters of about 25 nm, 280 nm, and 1780 nm.

9. A lipid microemulsion comprising:
   an aqueous phase comprising pluronic polyol at a concentration from 1% to 10% weight/volume in 10 ml of water; and
   a liquid organic phase dispersed in the aqueous phase comprising cod liver oil in an amount from 1 mg to 50 mg, polyoxyethylene (20) sorbitan monooleate in an amount from 0.5 mg to 75 mg, cholesterol in an amount from 2 mg to 7 mg, α-tocopherol acetate in an amount from 0.5 mg to 4 mg in 1 ml of ethanol wherein the microemulsion is free from serum albumin.

10. A lipid microemulsion comprising intact micelles stably dispersed in an aqueous phase, wherein the aqueous phase comprises a first emulsifier at a concentration from 1% to 10% weight/volume in 10 ml of water and the micelles comprise lipids and a second emulsifier in an amount from 0.5 mg to 75 mg in a 1 ml of liquid organic solvent wherein the microemulsion is free from serum albumin.

11. A lipid microemulsion as in claim 10, wherein the micelles are prepared by mixing a preformed organic solution of the lipids and second emulsifier with the aqueous phase.

12. A lipid microemulsion as in claim 10, wherein the lipids in the lipid component are selected from the group consisting of unsaturated fatty acids, mixtures of polyunsaturated fatty acid methyl esters, lipid soluble vitamins and sterols, wherein the organic solvent is a $C_1$–$C_3$ alcohol and wherein the first emulsifier or emulsifiers are selected from the group consisting of pluronic polyols and the second emulsifier or emulsifiers are selected from the group consisting of phospholipids and nonionic, nontoxic polymeric detergents.

13. A lipid microemulsion as in claim 2, wherein the lipids are selected from the group consisting of linoleic acid; linolenic acid; oleic acid; fish liver oil; vitamins A, B, and E; and cholesterol;

wherein the organic solvent is ethanol; and wherein the second emulsifier or emulsifiers are selected from the group consisting of lecithin and polysorbate compounds.

* * * * *